(12) United States Patent
Grinberg et al.

(10) Patent No.: US 11,534,609 B2
(45) Date of Patent: Dec. 27, 2022

(54) METHOD OF SEARCHING OPTIMAL ZONES FOR ELECTROPULSE THERAPY (VARIANTS)

(71) Applicant: RITM OKB ZAO, Taganrog (RU)

(72) Inventors: Yakov Zalmanovich Grinberg, Taganrog (RU); Yury Yurievich Starovoytov, Rostov-on-Don (RU); Mikhail Anatolievich Unakafov, Taganrog (RU)

(73) Assignee: RITM OKB ZAO, Taganrog (RU)

( * ) Notice: Subject to any disclaimer, the term of this patent is extended or adjusted under 35 U.S.C. 154(b) by 260 days.

(21) Appl. No.: 17/102,848

(22) Filed: Nov. 24, 2020

(65) Prior Publication Data
US 2021/0093860 A1 Apr. 1, 2021

Related U.S. Application Data

(60) Continuation-in-part of application No. 16/553,656, filed on Aug. 28, 2019, now abandoned, which is a division of application No. 16/077,641, filed as application No. PCT/RU2017/000080 on Feb. 17, 2018, now abandoned.

(30) Foreign Application Priority Data

Mar. 3, 2016 (RU) .......................... RU2016107880

(51) Int. Cl.
*A61N 1/36* (2006.01)
*A61N 1/04* (2006.01)
*A61B 5/053* (2021.01)
*A61B 5/316* (2021.01)
*A61B 5/25* (2021.01)

(52) U.S. Cl.
CPC ............ *A61N 1/3603* (2017.08); *A61B 5/053* (2013.01); *A61B 5/316* (2021.01); *A61N 1/0404* (2013.01); *A61N 1/36* (2013.01); *A61B 5/25* (2021.01); *A61N 1/36021* (2013.01)

(58) Field of Classification Search
CPC .... A61B 5/053; A61B 5/04012; A61N 1/3603
See application file for complete search history.

*Primary Examiner* — Alyssa M Alter
(74) *Attorney, Agent, or Firm* — Nadya Reingand

(57) ABSTRACT

The invention comprises providing electric stimuli, which are generated by forming the following ringing circuit: active electrode—inductive storage unit—passive electrode—interelectrode tissues—active electrode, the electric stimuli creating oscillations which are used as a test signal. In one variant of the method, the electrodes are successively applied (in another variant—moved uniformly) across the skin area. Every time the electrodes-to-skin contact is detected, the oscillation parameters are recorded after a delay. Moreover, the values of parameters can be averaged. The invention allows for both combined and disjointed (i.e. separated) electrode placement. An optimal zone for electropulse therapy is identified by a minimal or maximal value of one or more parameters of the aforementioned oscillations and the use of the principle of small asymmetry. The invention further provides for an increase in the accuracy with which zones optimal for electropulse therapy are identified and localized.

15 Claims, 5 Drawing Sheets

$1^{st}$ St – first stage of stimulus ('pumping')
$2^{nd}$ St – second stage of stimulus (free oscillations)
$U_a$ – amplitude of first pulse of the stimulus second stage

METHOD OF SEARCHING OPTIMAL ZONES FOR ELECTROPULSE THERAPY (VARIANTS)

CROSS-REFERENCE TO RELATED APPLICATIONS

This application is a Continuation-in-Part of U.S. patent application Ser. No. 16/553,656, which is a divisional application of U.S. patent application Ser. No. 16/077,641, filed Aug. 13, 2018, which in turn is a National Stage Patent application from PCT Application PCT/RU2017/000080, filed Feb. 17, 2018, which in turn claims priority to Russian Patent Application RU2016107880, filed Mar. 3, 2016.

FIELD OF THE INVENTION

The group of inventions refers to physiotherapy, in particular, the means of electropulse stimulation of the human skin by SCENAR devices and similar to those, in which the inductive energy storage unit is used for generating stimuli, and can be used in diagnostic, therapeutic, rehabilitation and preventive purposes.

BACKGROUND OF THE INVENTION

Currently, the stimulators using this principle are manufactured in Russia (SCENAR, DENAS, TINER, etc.) as well as in other countries (Interx, Avazzia, Physiokey, etc.).

An important aspect of the use of such stimulators is the search for the zones optimal for electric stimulation.

The use of inductive energy storage unit for stimuli generation allows to assess the reaction of the inter-electrode tissues (primarily skin) along with the stimulation, to evaluate the body's reaction to the stimulation in general, and thus, to evaluate the electrophysiological condition of a body.

From the summary and the description of the device in RU Patent No. 2068277, IPC 6 A61N1/36, published on 27 Oct. 1996, results a method, according to which the active and passive electrodes, connected to a switch amplifier with an output transformer, are placed on the patient's skin, the parameters of free oscillations that arise during that are measured, and body reaction to the stimulation is identified by the speed of changing of duration of the first half wave of the aforementioned oscillations, whereas the nature of pathology is identified by duration of the first half wave of these oscillations. (Free oscillations are mistakenly called forced oscillations in the description).

This method allows the evaluation of the body's reaction to the stimulation with the selected criteria, but does not provide for the search of zones optimal for electropulse therapy, which can be carried out using the same criteria by identifying the skin areas that are most different from those of the surrounding skin.

The drawback of this method is the considerable dependence of the parameters of free oscillations on the speed and force of the electrode pressing to the patient's skin, especially when the electrodes are being applied to the skin.

Their minor deviations may result in significant differences in the measured values of free oscillations parameters and, therefore, an incorrect identification of the body's reaction to the stimulation or the nature of pathology.

Another drawback of this method is the lack of averaging of measured values, which can also lead to a significant error in the evaluation of the body's reaction to the stimulation or the nature of pathology due to the high variability (dynamic properties) of the signal.

In addition, this method does not provide an evaluation of the body's reactions to the stimulation when the electrodes are moved along the skin.

The closest to the proposed one method of evaluating the electrophysiological condition of the human body is to apply electrodes to the skin, transmit an electric signal from high-quality inductor coil saturated with electromagnetic power through the interelectrode tissue, and use as a test signal the electric oscillations arising in the ringing circuit, formed by the following parts: active electrode—a high-quality inductor coil—passive electrode—interelectrode tissue—active electrode, an evaluation of the electrophysiological condition of the body by measuring the frequency, or amplitude, or damping of these oscillations (RU Patent No. 2161904 C2, A61V5/05, A61N 39/00, published on 20 Jan. 2001).

This method allows to perform the evaluation of the electrophysiological condition of the human body or, according to the description of the invention, of its particular organs and systems, using the results of measuring the parameters of free oscillations arising during the said stimulation.

Although this method does not support the searching of the optimal zones for electropulse therapy, it can also be used for these purposes by identifying the skin areas that are most different from the surrounding ones by the measurements of frequency, or amplitude, or damping of oscillations occurring in the aforementioned ringing circuit.

However, due to the lack of delay between the application of electrodes to the skin and the measurement of oscillations parameters, and also because there is no averaging of oscillation parameter values, this method cannot ensure the gage reproducibility in case of deviations in the speed of electrode application or the force of electrode pressing to the patient's skin.

Another drawback of this method is that it allows an evaluation of the electrophysiological state only in static condition, and does not allow it to be carried out when the electrodes are moved along the skin.

SUMMARY OF THE INVENTION

The aim to which the proposed invention is directed is to minimize the influence of such unavoidable subjective factors as non-uniformity of the speed of application and force of pressing of the electrodes on the skin on the results of measurement of parameters of free oscillations, which appear during the electropulse stimulation with stimuli generated by the inductive energy storage unit when searching for optimal zones for electropulse therapy by successive electrode applications.

As a result, the reliability of identification and accuracy of localization of optimal zones for electropulse therapy are increased when parameters of free oscillations are used for their searching.

The second aim to which the proposed invention is directed is to provide the possibility of searching optimal zones for the electropulse therapy during the labile method of stimulation, when the electrodes are moved uniformly across the entire surface of the chosen skin area.

The technical result of using the proposed method is the increasing of objectivity and accuracy in identifying the optimal zones for electropulse therapy by reducing the influence of subjective factors, and, also, providing the possibility of such search during labile stimulation.

The optimal zone for electropulse therapy is understood as the zone on the surface of a chosen treatment area of a subject's skin, which is most different from other parts of the same surface.

Several contiguous zones having equal parameter values should be considered as one zone.

If several non-contiguous zones with equal parameters are found, the smallest of them is considered as the optimal zone for stimulation.

The technical result of the invention is:

during the electrostimulation, which includes applying electrodes on the skin and transmitting electric pulses through the electrodes from inductive energy storage unit, the device's electrodes are successively placed across the entire surface of the chosen skin area and, after a set period between 0.1-0.5 sec following each detection of contact between the electrodes and the skin, the oscillation parameters are measured, and recorded, whereas the optimal zone for electropulse therapy is identified by a minimum or maximum measured value of one of the oscillation parameters or when the measured oscillation parameters reach a predefined criterion.

If several non-contiguous zones with equal measured extreme (i.e. minimum or maximum) parameter values, or otherwise equal criterion values, are found, they are not combined because they are not contiguous. Instead the smallest of them is considered as the optimal zone for stimulation.

The second variant, which modifies the step of successively placing, is the labile (i.e. movable) stimulation by electrodes of the entire surface of the chosen treatment area of a patient's skin. In this second variant, the electrodes are moved uniformly, and without being lifted off of the skin, across the chosen treatment area. If and when the chosen treatment area is too large such that it cannot be covered in one uniform movement, the electrodes are lifted off the skin at the end of a first portion of the chosen treatment area and reapplied to the skin at a beginning of the next portion. In such a case, the first portion (which may be the sole portion) should comprise at least one skin zone. When the chosen treatment area comprises multiple portions (i.e. at least a first and a second portion), the additional portions (i.e., second, third, fourth, and so on) may also comprise one or more skin zones. If new minimums/maximums are found in subsequent portions, a new optimal zone is detected; and if no new minimums/maximums are found in comparison to the parameter values from the first portion, then no new optimal zones are found. The entire surface of the chosen treatment area may thus be covered in one or more repetitions of uniformly moving the electrodes along a first portion of the skin, then a second portion of the skin, then a third portion, and so on, until the entire chosen treatment area is covered.

Similar to the first variant, in the second variant, after a set period of between 0.1-0.5 seconds following the detection of contact between the electrodes and the skin, the oscillation parameters are measured, and recorded. Sites/positions of the electrodes where minimums and maximums of one or more of the free oscillation parameters are found may be recorded as potential optimal zones. Alternatively, the sites/positions where a consistency of one or more of the free oscillation parameter values are detected are memorized as the optimal zone for the electropulse therapy (i.e., sites where parameter values reach a predefined range of a specific criterion, said parameter values remaining within that range, are memorized). It is further noted that since in this second variant the electrode(s) is(are) moved during measurement, the size of an optimal zone may initially be larger than the size of the electrode(s) themselves.

In either method, extremes or criteria can also be found for averaged parameter values. That is, measured parameter values may be further averaged, wherein said averaged measurements are also recorded. Averaging of the measured values further increases the accuracy of the data obtained such that an optimal zone for electropulse therapy may be identified. If averaging occurs, it is presumed that 2 or more values are obtained during said measuring, wherein the averaging is performed at the same time as the measuring.

If in any of these subvariants several non-contiguous zones with equal averaged extreme parameter values (instantaneous or averaged, respectively) or equal criterion values are found, the smallest of them is considered as the optimal zone for stimulation.

Both variants provide for the use of the combined electrode, containing both active and passive electrodes, and disjointed (separated, split) ones, where the active and passive electrodes are constructively separated, with one of them placed outside the chosen treatment area while the second one is applied or moved within it.

BRIEF DESCRIPTION OF THE DRAWINGS

The invention is explained by the following drawings.

DETAILED DESCRIPTION OF THE PREFERRED EMBODIMENT

Definitions.

"Chosen treatment area," as used herein, is defined as an entire even- or uniform-seeming area of the skin being examined (e.g., abdomen, back, neck-collar area, forearm, etc.).

"Skin zone" or "zone," as used herein, is defined as any site of skin covered during an instantaneous position of the electrode(s). A skin zone is simply any position of the electrodes on the skin at a given time. Several contiguous skin zones having equal parameter values should be considered as one skin zone.

"Optimal skin zone" or "optimal zone," as used herein, is defined as a skin zone located on the surface of a chosen treatment area of a subject's skin, said optimal skin zone being most different from other skin zones within the chosen treatment area. Influence on an optimal zone provides for the most effective therapy.

"Skin portion" or "portion," as used herein, is defined as a part of a chosen treatment area that is covered via a sliding movement of the electrode(s). Every skin portion may comprise any number of skin zones. Those skin zones which differ most from other skin zones within the chosen treatment area are identified as an optimal zone. If several contiguous (and perhaps overlapping) skin zones, located within one or more skin portions, have equal parameter values, those zones should be considered as one skin zone.

The first variant is to search the optimal zones for electropulse therapy by the successive placement of the electrodes.

It is known that when the electrodes contact the skin surface, which is generally a complex mixture of aqueous solutions, a number of processes occur at the "metal-solution" boundary.

This is, above all, the formation of the difference of potentials (double electric layer) called electrode potential (Grechin, V. (1997), "Neurophysiology techniques," Nauka, p. 7-9).

Figure 1:
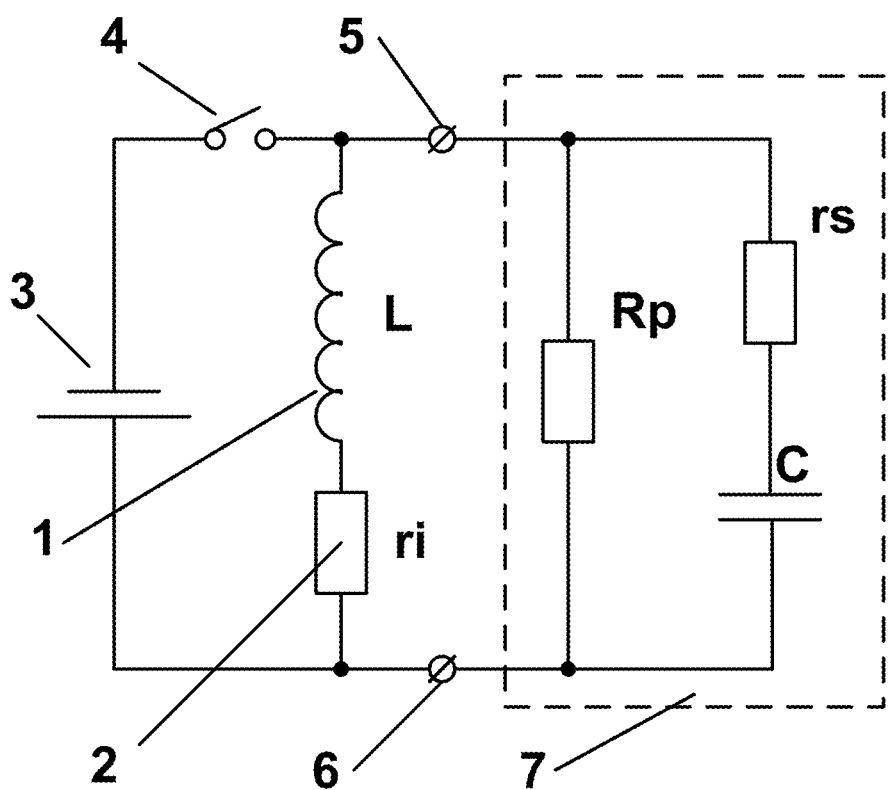
FIG. 1 is a functional diagram of the output stage of SCENAR device and the electrical equivalent of interelectrode tissues of the biological object.

The functional diagram of the output stage of the device, that influences the skin by the stimuli generated with the inductive storage unit, is shown in FIG. 1.

The output stage includes inductive energy storage unit 1 (i.e., "L") with internal active resistance 2 (i.e., "ri"), connected to the power supply 3 through switch 4 and to electrodes 5 and 6, which are placed on the tissue of the biological object 7, i.e. the interelectrode tissues—i.e., those tissues located between the two electrodes, the electric equivalent of which is presented by the RC circuit in FIG. 1 (see Popechitelev, E. P. and M. Kornevski, (2002), "Electricophysiological and photometric medical equipment. Theory and Design," Vysshaya Shkola, p. 64-65). This circuit 7 includes the Rp resistance, the double-layer capacity, C, and the interelectrode tissues' resistance, rs.

The interelectrode impedance for impulse current is almost entirely determined by the impedance of the double electric layer Rp and C, which changes over time during the formation of the aforementioned layer, both components are changed significantly and also quite quickly immediately after the electrodes are placed on the skin.

Figure 2:
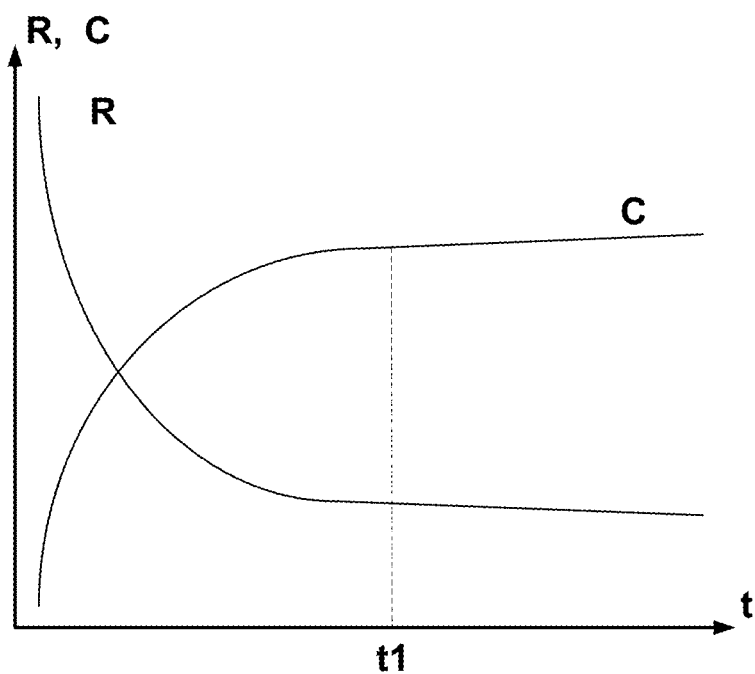
FIG. 2 illustrates the change of the capacity and active resistance of the double-layer over time.

A general view of change of Rp and C over time is shown on FIG. 2 (see Popechitelev, E. P. and M. Kornevski, (2002), "Electricophysiological and photometric medical equipment. Theory and Design," Vysshaya Shkola, p. 72).

On FIG. 2 the time of formation of the double-layer capacity is marked as t1.

After that, the changes of the double electric layer's impedance (Rp and C) are negligible and determined primarily by the electro-chemical reactions associated with the local metabolism under the electrodes.

The influencing stimuli are generated in the following way.

In the initial position, switch 4 is open.

When switch 4 is closed, the first stage of the stimulus generation begins, in which the voltage from power supply 3 is applied to the inductive energy storage unit 1, which causes a flow of a linearly increasing current through it, and, thus, the accumulation of electromagnetic energy by inductive energy storage unit 1.

That is, the energy is "pumping" into inductive energy storage unit 1, and, hence, the other name of the first stage of the stimulus is "pumping".

At this stage, the inductive energy storage unit 1 with active resistance, ri 2, as well as the power supply 3 with the switch 4 are connected in parallel to the interelectrode tissues 7, the interelectrode tissues thereby connecting the two electrodes to close the ringing circuit.

As the internal resistance of the power supply 3 and switch 4 (being around a few Ohms, these resistances are not shown on the diagram and may be ignored due to their small values) are significantly less than impedance of interelectrode tissues 7, the stimulus shape during the first stage is almost independent from the impedance of interelectrode tissues 7.

After the specified amount of power is reached, inductive energy storage unit 1 is disconnected from power supply 3, breaking switch 4.

The second stage of the stimulus generation begins, in the process of which the energy accumulated during the previous stage by inductive energy storage unit 1, is transferred through electrodes 5 and 6 to the tissues of biological object 7 and generates free electric oscillations in the ringing circuit, formed by the inductivity of the inductive energy storage unit 1 and the impedance of interelectrode tissues 7.

Now the small inner resistance 2 of the inductive energy storage unit 1 is connected sequentially with the impedance of interelectrode tissues 7, so the shape of the oscillations is completely determined by the impedance of interelectrode tissues 7 and the induction of the inductive energy storage unit 1.

The other name of the second stage is "free oscillations".

This method of creating of oscillations is known as "shock excitation", and the mentioned circuit is known as the shock-excited oscillatory circuit, or the ringing circuit.

Figure 3:
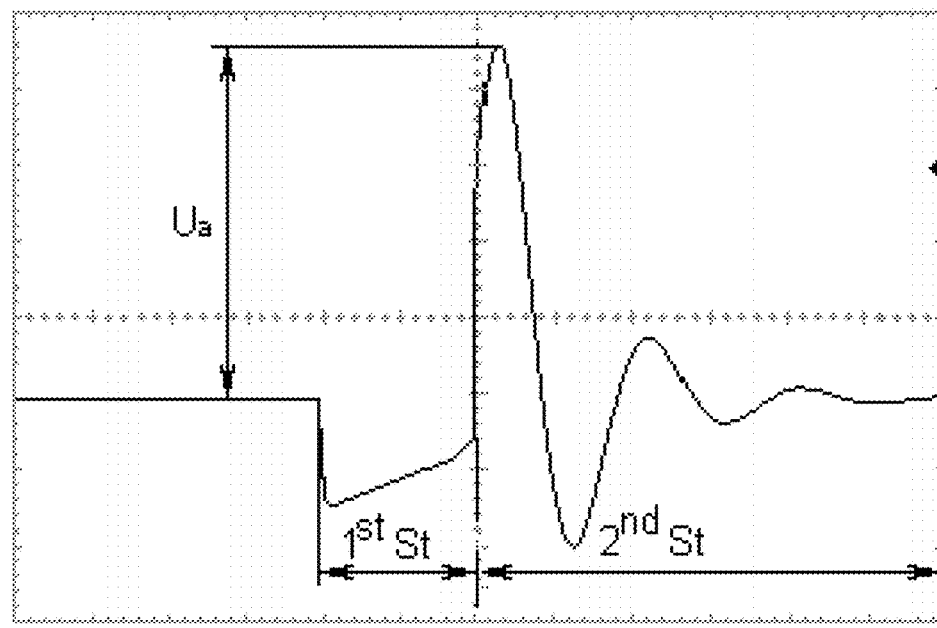
FIG. 3 illustrates an example of a stimulus shape.
Figure 4:
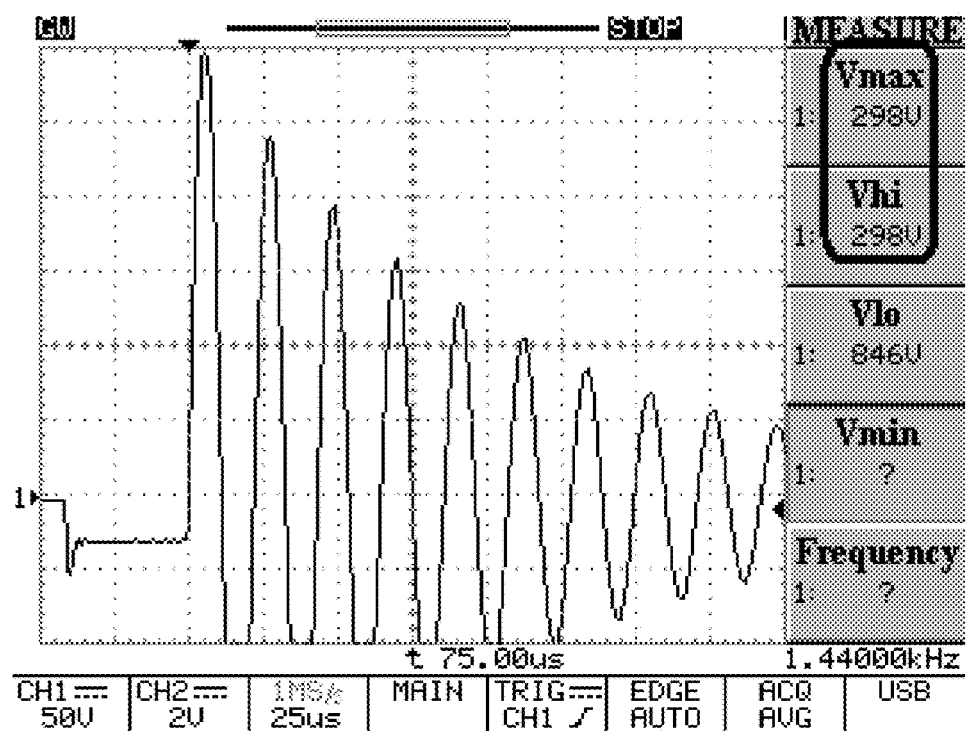
FIG. 4 illustrates the stimuli shape before the electrodes are applied to the skin.
Figure 5:
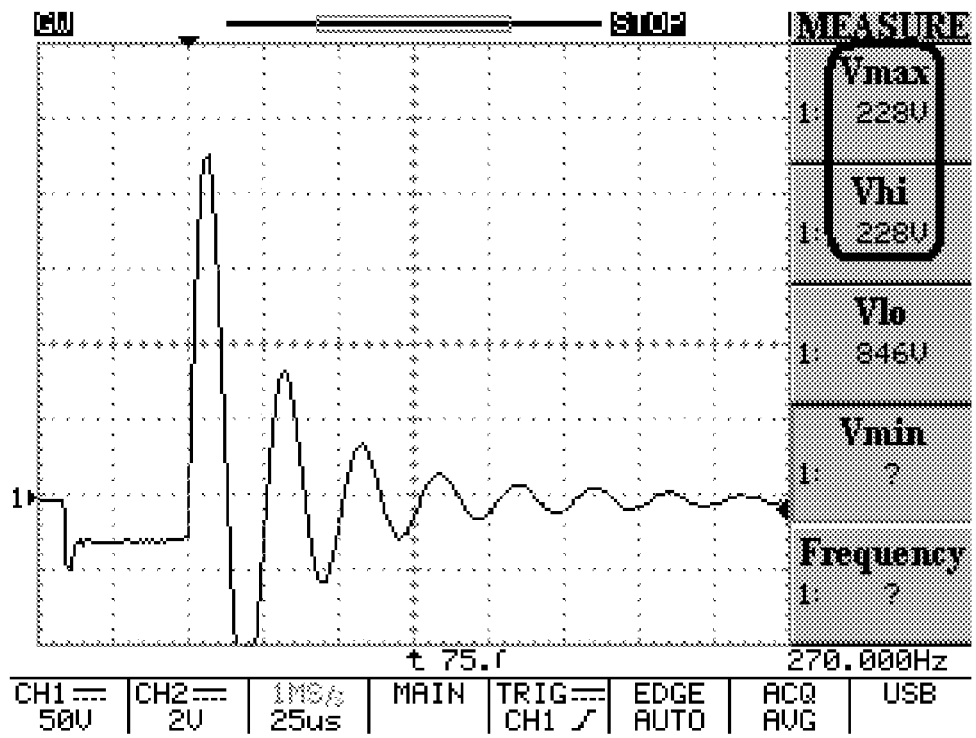
FIG. 5 illustrates the stimuli shape right after the electrodes are applied to the skin.
Figure 6:
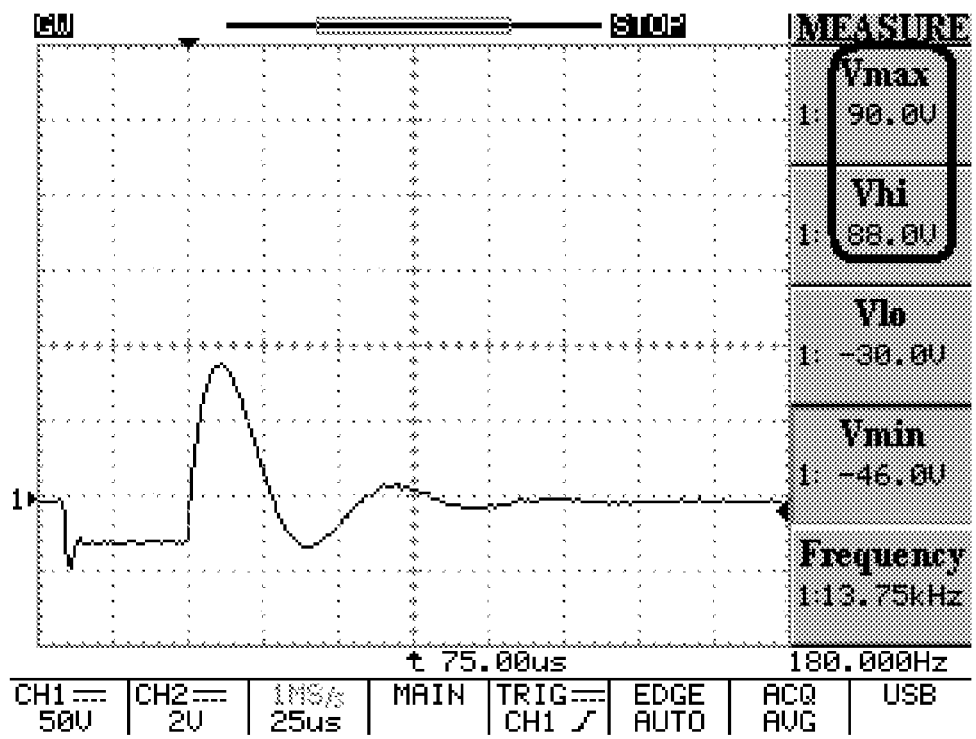
FIG. 6 illustrates the stimuli shape 5 seconds after the application of the electrodes to the skin.
Figure 7:
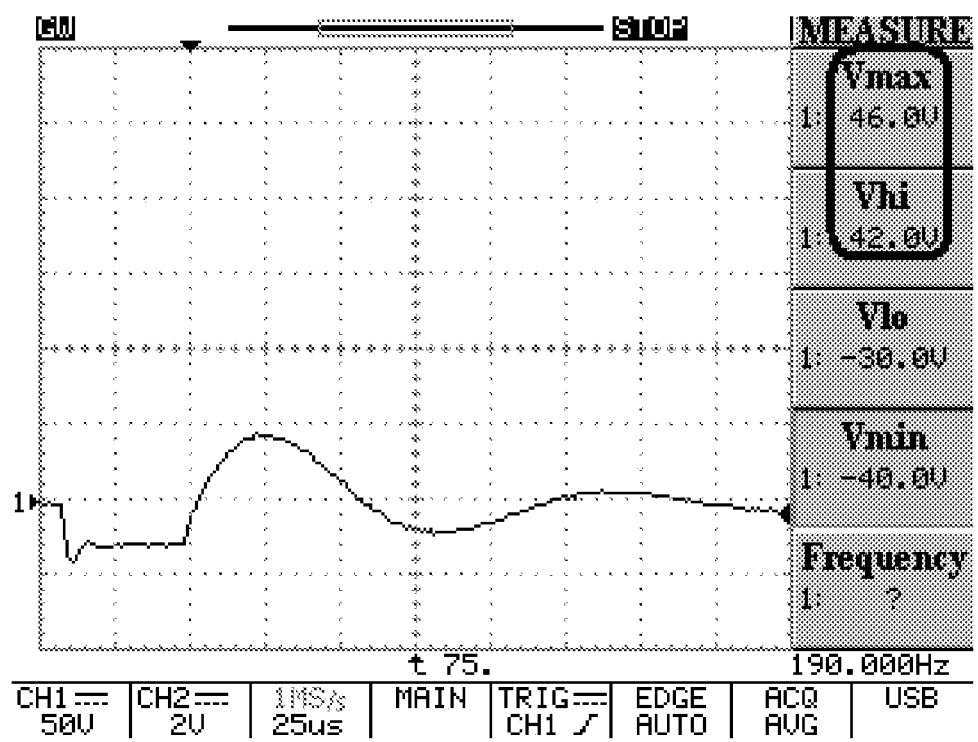
FIG. 7 illustrates the stimuli shape 30 seconds after the application of the electrodes to the skin.

An example of the shape of a two-stage stimulus generated with inductive storage unit is presented in FIG. 3.

To illustrate how changes of Rp and C affect the type of free oscillations, FIGS. 4-7 show stimuli oscillograms before the electrodes are applied to the skin, immediately after application, and 5 and 30 seconds after application, obtained when using the SCENAR device (Technical Conditions/TC 9444-015-05010925-2004).

From the presented oscillograms and graphs of changes of Rp and C, over time, it is clear that the parameters of free oscillations immediately after the electrodes are placed on the skin changes significantly, and the changes depend, also, on the speed of placing of the electrodes on the skin, and also on the degree and uniformity of the electrodes' pressure at each zone of the chosen treatment area.

Introduction of a certain constant delay between the primary (i.e. initial) contact of electrodes and skin and the beginning of measurement of free oscillations, which result will be used later to search for special zones allows to level the above factors to a large extent.

The delay duration must be sufficient to establish a firm contact between the electrodes and the skin, but not too large to provide for measurement on the initial area of graphs on FIG. 2, i.e. significantly before the t1 time expires.

Since this time is a few seconds, and the placing of the electrode on the skin from the first contact to dense pressing makes no more than 0.1-0.2 sec, it is reasonable to set the specified delay within 0.1-0.5 sec.

The averaging of the measured values further allows to additionally reduce dependence on the subjective factors of the electrode placing mentioned above.

As the measurements are conducted at the rate of stimuli generation, then the minimum averaging time is the double period of the stimuli sequence (for paired averaging), and the maximum one should not exceed the time of formation of the t1 double layer. After the double layer is achieved, the measured values are no longer relevant.

Thus, the averaging time should be within a range between several hundredths of a second and one or even two seconds. Averaged values can be presented to a doctor for later comparison or can be saved in the device's memory.

In a homogeneous section of the body (back, stomach, shoulder, forearm, neck-collar zone etc.), the optimal zones for electropulse therapy are identified by extreme deviation of one of the parameters of free oscillation from the other electrode placing or by achievement of a certain criterion on their basis.

Thus, an area of skin with maximum (or minimum) averaged duration of the first free oscillation (or its first half-wave, as described in RU Patent No. 2068277), or with maximum (or minimum) averaged duration of one of the subsequent free oscillations, or with maximum (or minimum) averaged number of free oscillations, or with maximum (minimum) change rate of the duration of the first free oscillation (or one of the subsequent oscillation) can be considered the optimal zone for electropulse therapy.

The skin area where the combination of measured parameters is reached can also be considered as the optimal zone for electropulse therapy.

More complex methods of zone identifying can be used on the basis of a predefined criterion—some predefined combination of values of measured (or averaged) oscillation parameters or the value of the oscillation parameter under certain condition.

For example, the criterion for selecting the optimal zone may be the maximum duration of the first free oscillation, with a minimum number of oscillations, or the maximum duration of the first free oscillation after the dynamics (change) of the oscillation has ceased.

As the proposed method for selecting optimal zones for the electropulse therapy uses extreme values of one of the free oscillations parameters, or reaching a certain criterion based on one or more oscillation parameters, then it is sufficient to indicate the moments of reaching the new extreme or the criterion rather than showing their values to a doctor.

In the simplest case, a doctor must memorize localization of only the last place where the extremes were reached, and it will be the optimal zone for the electropulse therapy.

If several zones with equal extreme parameter values are found, then in order to improve the efficiency of the therapy it is reasonable to treat not all of them, but only the so-called "small asymmetry" zones—the areas of skin surface which differ from the surrounding surface and which are small in relation to the entire surface treated (Gorfinkel, Y. (1996), "Theoretical and practical basis for improving the effectiveness of SCENAR therapy," SCENAR therapy and SCENAR Expertise collection 2: p. 16-18). The considered method of improving the effectiveness of therapy provides for the stimulation of only one of the found areas with equal extreme parameter values (or criterion), which is the smallest.

In the SCENAR therapy the labile stimulation is also applied, which facilitates the subjective determination of optimal zones for stimulation.

Therefore, the second variant is to search for special zones with the electrodes moved uniformly across the entire surface of the chosen skin area in one or more repetitions.

When the electrodes are moved on the skin, the same processes of double-layer formation occur, with the difference that new skin areas take part in the formation of the layer, while the treated ones are leaving the interelectrode space.

Thereby, the double-layer formation is not complete and the double-layer state is described as part of the graph on FIG. 2, located substantially to the left of the time t1.

In this case, the introduction of a constant delay between the electrode contact with the skin and the start of the measurement of free oscillations parameters will also allow to reduce the dependence of measured values on the subjective peculiarities of placing the electrodes on the skin.

After being firmly pressed on the skin the electrodes are moved within the selected zone.

When the size of the zone is significantly big (abdomen, back) then it is impossible to move the electrodes evenly on the entire surface with one movement.

The treatment of the zone with several movements of electrodes may also be provided for by methodological techniques.

In that case the surface is being treated with several movements in one direction (for example, from top to bottom) taking the electrodes off the skin and placing them back to the beginning of a new movement.

Introduction of a constant delay between the determination of the contact with the skin and the beginning of measurement of oscillation parameters when stimulating the zone, in one or more repetitions, allows to eliminate the error caused by nonuniformity of every placement of the electrodes on the skin until proper contact is achieved.

The measurements can be conducted at the stimuli rate, whereas the indication, as in the first variant, can be only made when a new extreme or criterion is reached.

To reduce the error caused by the uneven movement of electrodes, resulting in uneven change of impedance of Rp, C, and, consequently, uneven change of the parameters of free oscillations, it is useful to average the results of measurements.

The averaging can be carried out, e.g., with the several sequential measurements (simple averaging) or with a "sliding window" (moving averaging), or any other known methods.

The labile method also applies the principle of "small asymmetry", i.e. the impact on that identified zone with equal extreme parameter values, which is the smallest.

Both variants provide for the use of the combined electrode, containing both active and passive electrodes, as well as disjointed (separated) electrodes, where the active and passive electrodes are constructively separated. One of them is placed outside the zone selected for treatment, and the other is successively placed or moved within it.

The Proposed Method is Performed as Follows.

The electrodes are applied to the skin in an area close to the chosen treatment area, but outside of it.

The level of electrostimulation is set, for example, according to individual sensations, usually at a comfortable level.

The other electrostimulation parameters are also set manually or automatically in accordance with the selected therapy technique.

The method of searching optimal zones for electropulse therapy is chosen successively placing or labile/movable.

During the successively placing method of treatment, the electrodes are placed on the skin, and 0.1 to 0.5 sec after the detection of contact with skin (by measuring the parameters of free oscillations caused by formation of the dual-layer capacity, or by measuring the current flowing through the electrodes, or after stabilization of the force/pressure of the electrodes on the skin), the parameters of free oscillations are measured (and possibly averaged) during a set period, for example, 1 second.

The stimulation is then stopped, and, in the simplest case, the doctor is provided with result of the measurement of oscillations parameters or the calculated value of the criterion.

The electrodes are then taken off the skin (the device is removed from the skin) and placed onto the next zone of the chosen treatment area.

By comparing the received values (numerical or mnemonic, for example, the brightness of the glowing LED, or the number of LEDs glowing, or pitch of the sound tone, or the clicking sound rate), the doctor identifies the zones optimal for electropulse therapy.

In order to eliminate redundant information during the next successive placings of the electrodes, only the information about the achievement of a new extreme (or criterion) can be provided, whereas it is enough to indicate the end of the averaging time if no new extremes (or criterion) have been achieved at the new placing point.

The device itself can record the extreme zones by identifying them, for instance, with the sequential index of the electrode placing.

It is also possible to make a video recording of the electrodes application points and to link the measured values to them.

When a computer is used for these purposes, the identification of zones optimal for electropulse therapy and their localization can be fully automated.

According to the results of the optimal zone identification, after searching through the entire chosen treatment area, the main therapy is carried out, according to the chosen technique, at the optimal zone.

If several non-contiguous equal value zones were found, then the smallest of those zones is considered as the optimal zone for electropulse therapy.

During the labile method of searching, after setting the individual level and parameters of electrostimulation as described above, the electrodes are placed on the chosen treatment area and moved uniformly within a first portion of the chosen treatment area (i.e. along the skin without lifting the electrodes until an end of the first portion is reached).

0.1-0.5 sec after detecting contact with the skin, the parameters of free oscillations begin to be measured (and averaged, if averaging is performed), presenting the doctor the results of measurement or the calculated values of the criterion. After the electrodes are uniformly moved across the entire first portion, the electrodes are lifted from the skin and repositioned at a beginning of the second portion within the chosen treatment area. The repositioning acts as a new detection of contact with the skin, which initiates a new 0.1-0.5 second pause prior to any measuring occurring along the second portion. Third, fourth, fifth, etc., portions of a chosen treatment area should be treated in a similar manner.

When direct measurements are used (without averaging), the elimination of redundant information is more important than during the successively placing method of treatment, that is why only the moments of achievement of new extremes are indicated for the labile method (e.g., in one of the above mentioned ways).

During the averaging of results (using either method), either all the results may be presented, or only the moments of achievement of new extremes.

Since there is no link between the sequential index of the electrode placing point and the treatment area in this case, recording the data by device is ineffective and the doctor should remember the place of achievement of the new extreme.

All other ways of automating the successively placing method of treatment (video recording or recording data and locations of the electrodes by a computer) are applicable to the labile method.

According to the results of the optimal zone identification, after searching through the entire chosen treatment area, the main therapy is carried out, according to the chosen technique.

If several non-contiguous equal value zones are found then the treatment of the smallest zone is conducted.

The use of separated electrodes in both variants of the method is similar to the aforementioned, with the only difference being that the passive electrode is fixed in place on the skin outside the chosen treatment area, whereas the search within the chosen treatment area is carried out with the active electrode.

INDUSTRIAL APPLICABILITY

The group of inventions may be used in the treatment of various diseases, first of all, pain syndromes, regardless of their etiology, by stimulators which use inductive energy storage unit to generate stimuli and reduce the time of the procedures, improving the effectiveness of the treatment at the same time.

Continued Description. As noted throughout this application, two methods for applying electrodes to the tissue are provided in the instant application. The first of these methods is the "successive placing" method. The second of these methods is the "labile/movable" method, which modifies the first method. "Successive placing" is defined as a method comprising the positioning of one electrode (i.e., the active electrode) or both electrodes onto the skin of a patient, at a first skin zone within a chosen treatment area, obtaining measurements without lifting or moving/sliding the electrode(s), then lifting the electrode(s) off of the skin of the patient, and finally positioning the active or both electrodes onto a next skin zone. The next skin zone will be within the same chosen treatment area, e.g., a section of the skin adjacent to the first skin zone. This process may be repeated successively any number of times, as required based on the size of the chosen treatment area.

In contrast, the "labile/movable" method is defined as a method which modifies the "successive placing" method by substituting a sliding movement along the skin and after contact between the electrode(s) and the skin, such that an entire portion of a chosen treatment area, and perhaps the entire chosen treatment area, may be covered without lifting the electrodes. In contrast, the "successive placing" method does not provide for any sliding movement of the electrode(s) along the skin. Thus, the "labile/movable" method further includes the feature that during each contact between the active or both electrodes with skin within the chosen treatment area, the active electrode or both electrodes are moved along (i.e. slid along) a first portion of the chosen treatment area, without lifting the electrode(s) but while sliding the electrode(s) (i.e., maintaining contact between the electrode(s) and the skin), thereby covering the entire first portion. In cases where the first portion is the entire chosen treatment area, the process ends after the first portion is sufficiently covered.

When the chosen treatment area comprises multiple portions (i.e. at least a first and a second portion), the additional portions (i.e., second, third, fourth, and so on) may also comprise one or more skin zones. If new minimums/maximums are found in subsequent portions, a new optimal zone is detected; and if no new minimums/maximums are found in comparison to the parameter values from the first portion, then no new optimal zones are found. Therefore, in the second variant and with multiple portions, once the first portion is covered, the active electrode or both electrodes are lifted from the skin and repositioned at a beginning of a second portion of the chosen treatment area. From here, the active or both electrodes are moved within the second portion, similarly sliding along the skin while continuously maintaining contact with the skin, until the end of the second portion, then to a third portion, and so on (e.g., from a first portion, to a second portion, to a next portion, and so on, until all portions of the entire chosen treatment area are covered).

The measuring of free oscillation parameters induced by the inductive storage unit is performed after contact between the electrodes and the interelectrode tissues. The measuring is preferably not taken into consideration during an initial period of contact between the electrode(s) and the skin. Therefore, a pause is provided, said pause comprising 0.1-0.5 second immediately following a detection of initial contact between the skin and the electrode(s). The pause is provided to avoid measurements which might be made after first contact but prior to the establishment of stable contact (i.e. sufficient contact) between the electrode(s) and the skin. The pause thereby avoids the consideration of irrelevant values which might otherwise be considered during the time period between "initial contact" and "stable contact" between the electrodes and the skin. The pause ensures that, prior to initiating the measuring of any parameter (or at least prior to displaying, or prior to averaging) of the free oscillations induced by each stimulus, a sufficient contact between the skin and the electrode has been established, and therefore unstable oscillation parameter values are not measured, recorded, displayed, etc. The pause is particularly optimal when averaging of the measured parameters is also provided, since the pause removes any unwanted measurement values from the average calculation, thereby making the average calculation more accurate.

The process of the pause is further detailed as follows: Stimuli are provided via the inductive energy storage unit at all times; for the "successive placing" variant (i.e. first variant): (1) once the electrodes are placed in a desired position (i.e., on a first skin zone of the chosen treatment area), an initial (i.e. first) contact is detected between the electrodes and the interelectrode tissues (i.e., those tissues of the patient located between the two electrodes); (2) after the initial contact is detected, a pause is provided for 0.1-0.5 seconds; (3) after the pause, free oscillation parameter measurements are performed; (4) free oscillation parameters measurements may further be averaged for one or more parameter values; (5) the measured or averaged parameter values are recorded; (6) the electrodes are transferred to a next skin zone and the process starts anew from step (1), with the electrode(s) being positioned in the second zone instead of the first zone. In the final step of the process, the electrodes are removed from the final zone rather than being placed onto a sequential zone.

The labile/moveable variant (i.e. second variant) comprises a difference in that the electrode(s) can slide along one or more portions of the chosen treatment area. Thus, the initial (i.e. first) contact is detected only once, i.e., at a beginning of every portion of the chosen treatment area. Hence, for the labile/moveable variant, the steps of the process are as follows: (1) once the electrodes are placed in a desired position (i.e., on a beginning of a first skin portion of the chosen treatment area), an initial (i.e. first) contact is detected between the electrodes and the interelectrode tissues (i.e., those tissues of the patient located between the two electrodes); (2) after the initial contact is detected, a pause is provided for 0.1-0.5 seconds; (3) free oscillation parameter measurements are performed; (4) free oscillation parameters measurements may further be averaged for one or more parameter values; (5) the measured or averaged parameter values are recorded; (6) the electrode(s) is moved along the first skin portion away from the beginning of the first skin portion and towards an end of the first skin portion but within the chosen treatment area, without lifting the electrode(s) from the skin, and the process starts anew from step (3). In the final step of the process, when the first skin portion has been sufficiently covered, the electrodes are removed from the skin (and potentially re-positioned at a beginning of a next (e.g. second) skin portion, at which point the process begins anew from step (1)). Recorded parameter values are compared during movement of the electrodes along the skin to determine the optimal zone for electropulse therapy.

Alternatively, the measurements of free oscillation parameters may occur directly following each detection of contact with the patient's skin, or even at all times. If such is the case, however, the displaying of the measured parameters, as well as any averaging of measured parameters, are the steps which would initiate after the 0.1-0.5 second pause, so as not to include measured values during the time of the pause in any recording, displaying, averaging, or calculating step utilizing the measured parameters occurring prior to establishing proper contact.

Figure 8:
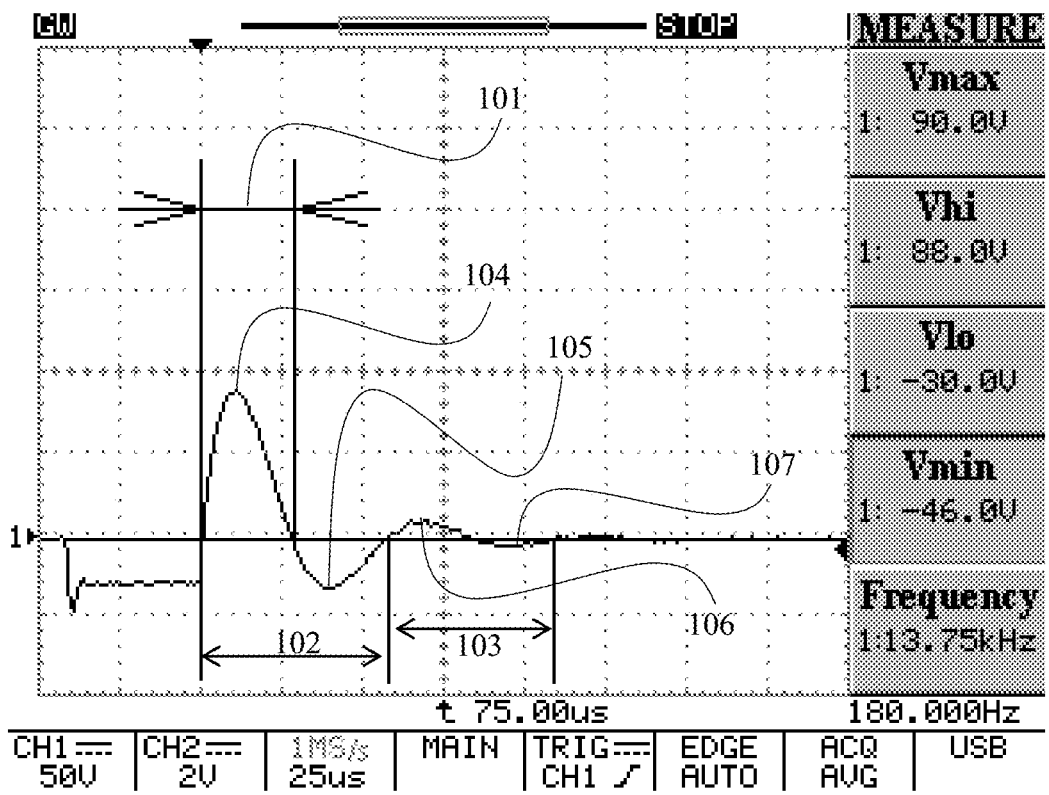
FIG. 8 illustrates examples of measured parameter values, according to the present invention.
Figure 9:
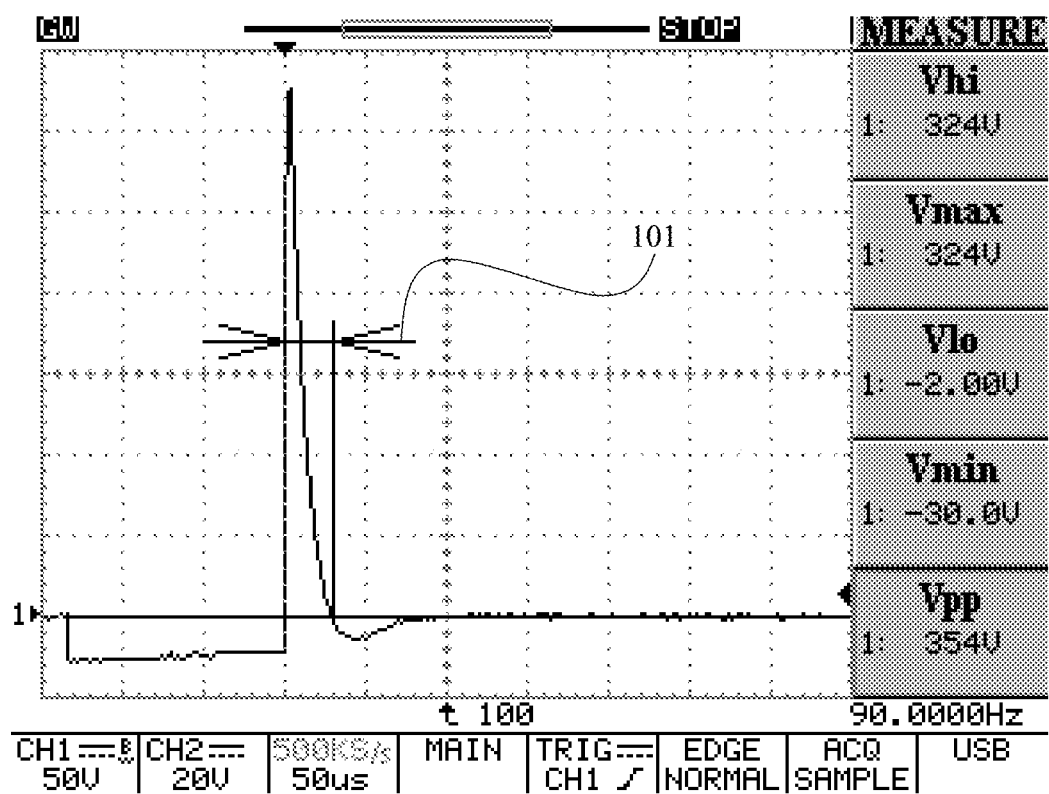
FIG. 9 further illustrates the parameter value of the first half-wave of free oscillations, wherein the first half-wave is the only half-wave, as measured according to the present invention.

Measured free oscillation parameters include but are not limited to the following (see, e.g., FIGS. 3, 8, and 9):

(1) an amplitude of the first half-wave of the free oscillations (see, e.g., FIG. 3, labelled $U_a$);

(2) a duration of the first half-wave of the free oscillations 101 (See FIG. 8, which shows via example a stimulus shape with several free oscillations, and FIG. 9, which shows via example a stimulus shape with only one free oscillation);

(3) a total number of full waves of the free oscillations or a total number of half-waves of the free oscillations (See FIG. 8, which shows via example an oscillation with a first full wave 102 and a second full wave 103; FIG. 8 further shows a first half-wave 104, a second half-wave 105, a third half-wave 106, and a fourth half-wave 107);

(4) a speed of changing of duration of the first half-wave of the free oscillations (i.e. a rate of change of the durations of each first half-wave of free oscillations);

(5) a rate of change of one or more free oscillation parameters;

(6) a combination of free oscillation parameters reaching a predefined criterion.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method of searching for optimal zones for electropulse therapy, comprising:
applying an active electrode and a passive electrode on a first zone of a chosen treatment area,
generating electric pulses using an inductive energy storage unit connected to said active and said passive electrodes,
said electric pulses causing free electrical oscillations in a circuit comprising said inductive energy storage unit, said active electrode, and said passive electrode, and tissues of said first zone located between said active and said passive electrodes,
using said free electrical oscillations as a test signal,
measuring parameters of said free electrical oscillations, said measuring being performed 0.1-0.5 seconds following each detection of initial contact between said active and said passive electrodes and said tissues,
displaying said measured parameters of said free electrical oscillations via a display means,
removing said active and said passive electrodes from said first zone,
successively placing said active and said passive electrodes onto a next zone of said chosen treatment area, repeating said measuring and said displaying steps at said next zone,
comparing said displayed parameters during every step of said successively placing, and
identifying an optimal zone for electropulse therapy based on one or more of said displayed parameters.

2. The method of claim 1, wherein said identifying an optimal zone for electropulse therapy is based on a maximum value of one of said displayed parameters.

3. The method of claim 1, wherein said identifying an optimal zone for electropulse therapy is based on a minimum value of one of said displayed parameters.

4. The method of claim 1, wherein said identifying an optimal zone for electropulse therapy is based on when one or more of said displayed parameters reach a predefined criterion.

5. The method of claim 1, further comprising:
averaging said measured parameters of said free electrical oscillations, and
displaying said averaged parameters via said display means.

6. The method of claim 1, wherein said identifying an optimal zone for electropulse therapy further comprises:
providing a determination, when two or more zones within a chosen treatment area have equal values of said displayed parameters, of a smallest one of said zones as said optimal zone for electropulse therapy.

7. A method of searching for optimal zones for electropulse therapy, comprising:
applying an active electrode on a first zone of a chosen treatment area, and applying a passive electrode outside said chosen treatment area,
generating electric pulses using an inductive energy storage unit connected to said active and said passive electrodes,
said electric pulses causing free electrical oscillations in a circuit comprising said inductive energy storage unit, said active electrode, and said passive electrode, and tissues located between said active and said passive electrodes,
using said free electrical oscillations as a test signal,
measuring parameters of said free electrical oscillations, said measuring being performed 0.1-0.5 seconds following each detection of initial contact between said active electrode and said tissues,
displaying said measured parameters of said free electrical oscillations via a display means,
removing said active electrode from said first zone,
successively placing said active electrode onto a next zone of said chosen treatment area, repeating said measuring and said displaying steps at said next zone,
comparing said displayed parameters during every step of said successively placing, and
identifying an optimal zone for electropulse therapy based on one or more of said displayed parameters.

8. A method of searching for optimal zones for electropulse therapy, comprising:
applying an active electrode and a passive electrode on a beginning of a first portion of a chosen treatment area,
generating electric pulses using an inductive energy storage unit connected to said active and said passive electrodes,
said electric pulses causing free electrical oscillations in a circuit comprising said inductive energy storage unit, said active electrode, and said passive electrode, and tissues of said first portion located between said active and said passive electrodes,
using said free electrical oscillations as a test signal,
measuring parameters of said free electrical oscillations, said measuring being performed 0.1-0.5 seconds following each detection of initial contact between said active and said passive electrodes and said tissues,
displaying said measured parameters of said free electrical oscillations via a display means,
sliding said active and said passive electrodes from said beginning of said first portion to an end of said first portion, repeating said measuring and said displaying steps during said sliding,
comparing said displayed parameters during every step of said sliding, and
identifying an optimal zone for electropulse therapy based on one or more of said displayed parameters.

9. The method of claim 8, further comprising:
applying said active and said passive electrodes onto a beginning of a next portion of the chosen treatment area, and
repeating said sliding, said measuring, and said displaying from said beginning of said next portion to an end of said next portion.

10. The method of claim 8, wherein said identifying an optimal zone for electropulse therapy is based on a maximum value of one of said displayed parameters.

11. The method of claim 8, wherein said identifying an optimal zone for electropulse therapy is based on a minimum value of one of said displayed parameters.

12. The method of claim 8, wherein said identifying an optimal zone for electropulse therapy is based on when one or more of said displayed parameters reach a predefined criterion.

13. The method of claim 8, further comprising:
averaging said measured parameters of said free electrical oscillations, and
displaying said averaged parameters via said display means.

14. The method of claim 8, wherein said identifying an optimal zone for electropulse therapy further comprises:
providing a determination, when two or more zones within a chosen treatment area have equal values of said displayed parameters, of a smallest one of said zones as said optimal zone for electropulse therapy.

15. A method of searching for optimal zones for electropulse therapy, comprising:
applying an active electrode on a beginning of a first portion of a chosen treatment area, and applying a passive electrode outside said chosen treatment area,
generating electric pulses using an inductive energy storage unit connected to said active and said passive electrodes,
said electric pulses causing free electrical oscillations in a circuit comprising said inductive energy storage unit, said active electrode, and said passive electrode, and tissues located between said active and said passive electrodes,
using said free electrical oscillations as a test signal,
measuring parameters of said free electrical oscillations, said measuring being performed 0.1-0.5 seconds following each detection of initial contact between said active electrode and said tissues,
displaying said measured parameters of said free electrical oscillations via a display means,
sliding said active electrode from said beginning of said first portion to an end of said first portion, repeating said measuring and said displaying steps during said sliding,
comparing said displayed parameters during every step of said sliding, and
identifying an optimal zone for electropulse therapy based on one or more of said displayed parameters.

* * * * *